(12) United States Patent
Gleason (10) Patent No.: US 6,695,852 B2
(45) Date of Patent: Feb. 24, 2004

(54) TENSION TOOLS FOR TENSION BAND CLIP

(75) Inventor: Joseph E. Gleason, Eagan, MN (US)

(73) Assignee: Spineology, Inc., Stillwater, MN (US)

( * ) Notice: Subject to any disclaimer, the term of this patent is extended or adjusted under 35 U.S.C. 154(b) by 144 days.

(21) Appl. No.: 10/000,770

(22) Filed: Oct. 31, 2001

(65) Prior Publication Data

US 2003/0083669 A1 May 1, 2003

(51) Int. Cl.$^7$ .............................................. A61B 17/58
(52) U.S. Cl. .................. 606/103; 606/148; 606/144; 606/139
(58) Field of Search .............................. 606/60, 61, 72, 606/74, 86, 102, 103, 140, 142, 144, 148, 151, 157, 158, 228

(56) References Cited

U.S. PATENT DOCUMENTS 3,507,270 A * 4/1970 Ferrier ........................ 600/481
4,966,600 A 10/1990 Songer et al.
5,456,722 A 10/1995 McLeod et al.
5,628,756 A 5/1997 Barker, Jr. et al.
6,053,921 A 4/2000 Wagner et al.

FOREIGN PATENT DOCUMENTS

| DE | 197 16 504 A1 | 12/1998 |
| EP | 0 625 336 A2 | 11/1994 |
| WO | 9522294 A | 8/1995 |

* cited by examiner

*Primary Examiner*—Cary E. O'Connor
*Assistant Examiner*—Candice C. Melson
(74) *Attorney, Agent, or Firm*—Vidas, Arrett & Steinkraus PA (57) ABSTRACT

A tensioning tool which holds the free ends of a tension band secured to a clip and clip screw and rotation of an adjusting knob causes tension to be applied to pull the band through the clip until the desired tension is achieved.

5 Claims, 8 Drawing Sheets

TENSION TOOLS FOR TENSION BAND CLIP

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to a tensioning tool used with a tension band and clip system in spinal applications. The tensioning tool assists in the placement of the tension band and its corresponding clip. Once positioned, the tensioning tool pulls on the tension band through the clip and holds it while the clip is locked securely with the clip screw.

Surgical procedures for the repair or fusion of large and small bones, ligaments and tendons, and other orthopedic procedures frequently require use of an orthotic device or attachment apparatus which can be subject to tensioning and bear heavy loads caused by the unique anatomical features of the compromised bone or tendon. For example, fractures of the patella are exposed to high stresses during flexion and extension of the knee joint; fusions of the spinal vertebrae are exposed to high gravitational forces and movements of the spinal column; torn ligaments and tendons are exposed to high stresses due to contraction of the associated muscle or flexion and extension of the bony structures; and trochanteric reattachment and cerclage techniques involve cable that is tensioned and exposed to high weight loads and stress factors.

Examples of surgical cable attachments include U.S. Pat. No. 4,966,600 to Songer et al. Clamps for holding the cables are shown in U.S. Pat. No. 6,053,921 to Wagner et al. A polyethylene cable system is described in U.S. Pat. No. 5,456,722 to McLeod et al. Polyethylene cable tying is shown in U.S. Pat. No. 5,628,756 to Barker Jr., et al.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

The invention provides a tensioning tool for use with a clip designed to grip and hold a tension band or cable without the use of any additional securing features such as knots, such as the clip shown and described in U.S. Provisional Patent Application No. 60/242,841 filed Oct. 24, 2000, the disclosure of which is incorporated by reference. It is especially well suited for use with braided polymeric cable. It employs a tapered screw concept which is customized using radii at both the root and crest of the thread. This prevents cutting of the cable. Standard clip designs using sharp teeth would cut individual cable strands leading to cable failure.

The clip design allows for easy engagement (starting of the thread) with progressively more compression of the braided cable. The female thread of the outer body is designed with a large radius where the cable exits to form a loop. The thread profile follows the main taper and thus blends gradually to zero depth. This, along with the large exit radius, minimizes all sharp bends which act to cut the cable under cyclic loading.

The tensioning tool is used with a clip through which the tension band ends are placed after the tension band is positioned over the body parts, such as adjacent spinous processes. The ends of the tension band are secured to pins on the tool and a tension shaft of the tool is driven downwardly away from the pins, increasing the distance from the pins to the clip, thereby tightening the bands. Once tightened as desired, a tension wrench is inserted through the tool with a clip screw positioned on its tip. It is then rotated until the screw is firmly seated in the clip, thereby trapping the band in between the clip and screw. The tool is then removed after releasing the band ends from the pins. Any excess band ends may be trimmed away.

BRIEF DESCRIPTION OF THE DRAWINGS

A detailed description of the invention is hereafter described with specific reference being made to the drawings in which.

DETAILED DESCRIPTION OF THE INVENTION

The tensioning tool 10 in the figures includes a tension main body 12, a tie off slider 14, adjustment knob 16 and clip screw wrench 18. The tie off slider 14 is slid onto the main body 12 of the device. Flats 20 on the main body 12 interface to flats 22 on the tie off slider 14 preventing it from rotating with respect to the main body 12. The tension spring 24 is slid into the cylinder 26 of the tie off slider 14, and over the cylinder 28 of the main body 12. The retaining lock 30 follows the same path as the spring 24 to lock it into place. The retaining lock 30 has keys 32 which interface to the main body slots 34 The retaining lock 30 is pushed against the spring 32 into the slots 34 and turned once bottomed out. In the turned position, the spring 24 pushes the keys 32 into the slot pockets. This prevents the retaining lock 30 from coming off.

The adjusting knob 16, with its annular ring 36, is slid into a T-slot 38 of the main body 12. The tensioning shaft 40 is slid into the end of the main body 12. The tension shaft 40 has flats 42 on the outside diameter which interface to flats 20 on the inside diameter of the main body 12 preventing it from rotating with respect to the main body 12 while allowing it to slide freely through the main body 12. Left hand threads 44 on the outside diameter of the tension shaft 40 interface to left hand threads 46 on the inside diameter of the adjusting knob 16. Turning the adjusting knob 16 counterclockwise draws the tension shaft 40 into the main body 12 and readies it for use.

The loop system is comprised of a tension band 50, female clip 52, and a male clip lock 54. The tension band 50 is routed inter body as required, and then the ends 56, 58 are fed through the female clip 52. The loose ends 56, 58 of the tension band 50 are fed through the slot 60 of the tensioning shaft 40 and then back out to the outside of the shaft through reliefs 62 in the shaft for routing up to the tie offs 64 on the sliding tie off 14.

After the tension band 50 has been routed and tied off on both sides, tension can begin by turning the adjusting knob 16 clockwise driving the tensioning shaft 40 out of the main body 12. As tension builds, the tension shaft 40 will pull on the sliding tie off 14, pulling it off the main body 12. In doing so, it will compress the spring 24 between it and the retaining lock 30. This relative movement between the sliding tie off 14 and the main body 12 can be seen as the retaining lock 30 migrates into the sliding tie off 14 as observed through a slot 70 in the sliding tie off 14. The distance traveled is proportional to the force applied and the spring rate of the spring 24. A scale marking on the sliding tie off can show the minimum and maximum forces.

Once engaged, the adjusting knob 16 cannot slide back out of the T-slot 38 of the tension body 12. The adjusting knob 16 and tension shaft 40 are hollow. This allows the clip screw wrench 18 to be passed through the adjusting knob 16 and the tension shaft 40 when securing a clip screw lock 54 into a clip 52.

Figure 1:
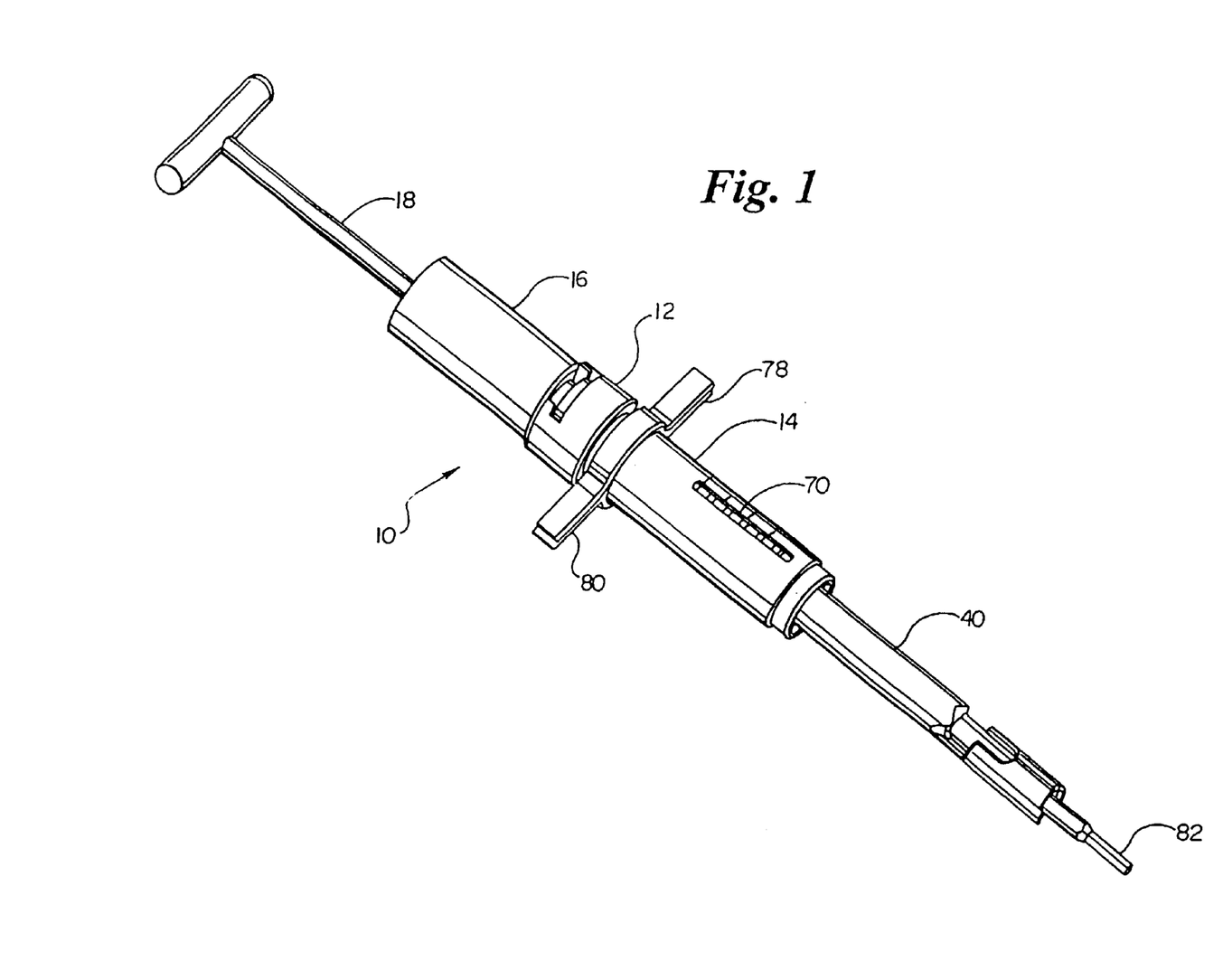
FIG. 1 is a perspective view of the tool of the invention.
Figure 2:
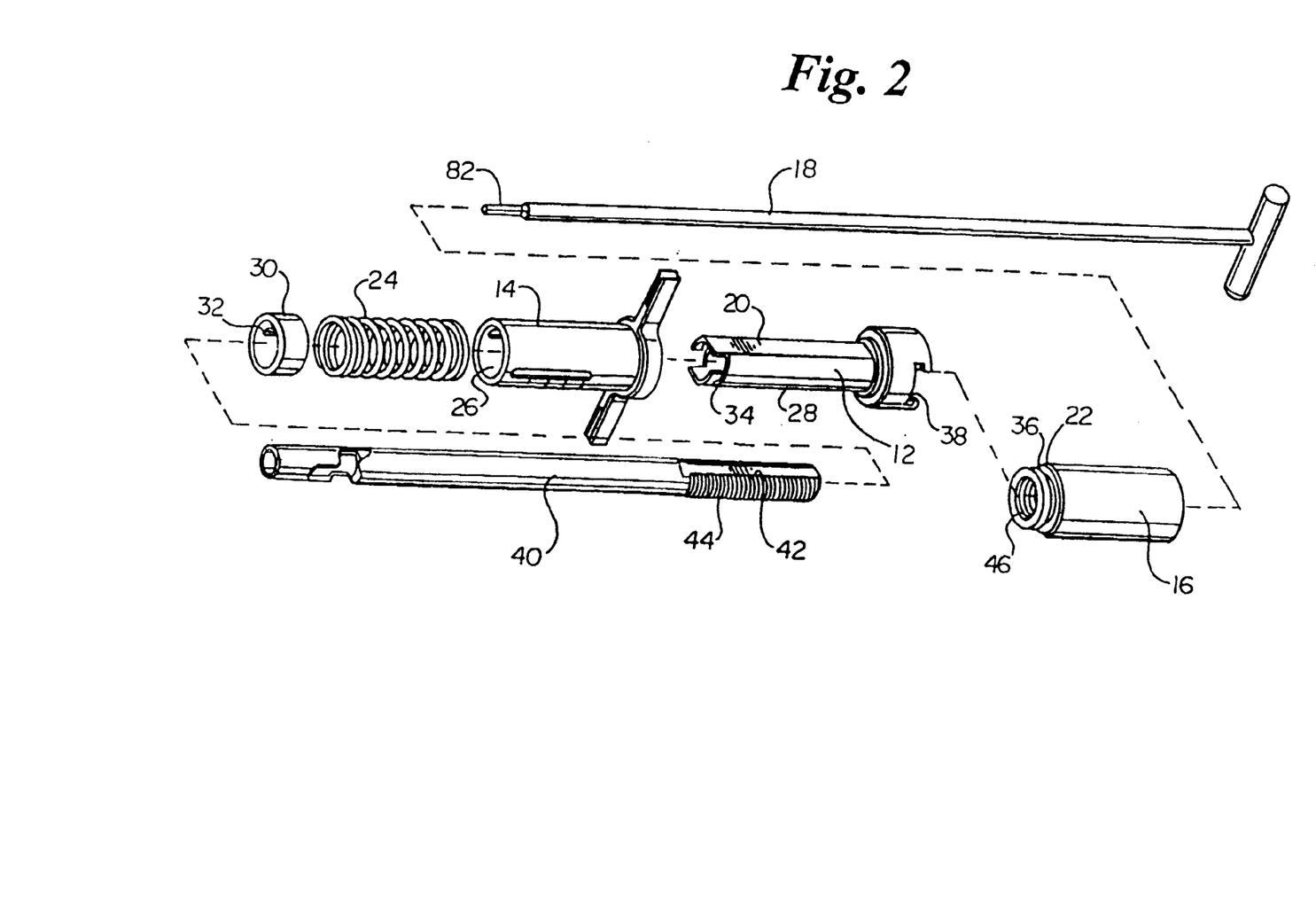
FIG. 2 is an exploded perspective view of the tool.
Figures 3, 4:
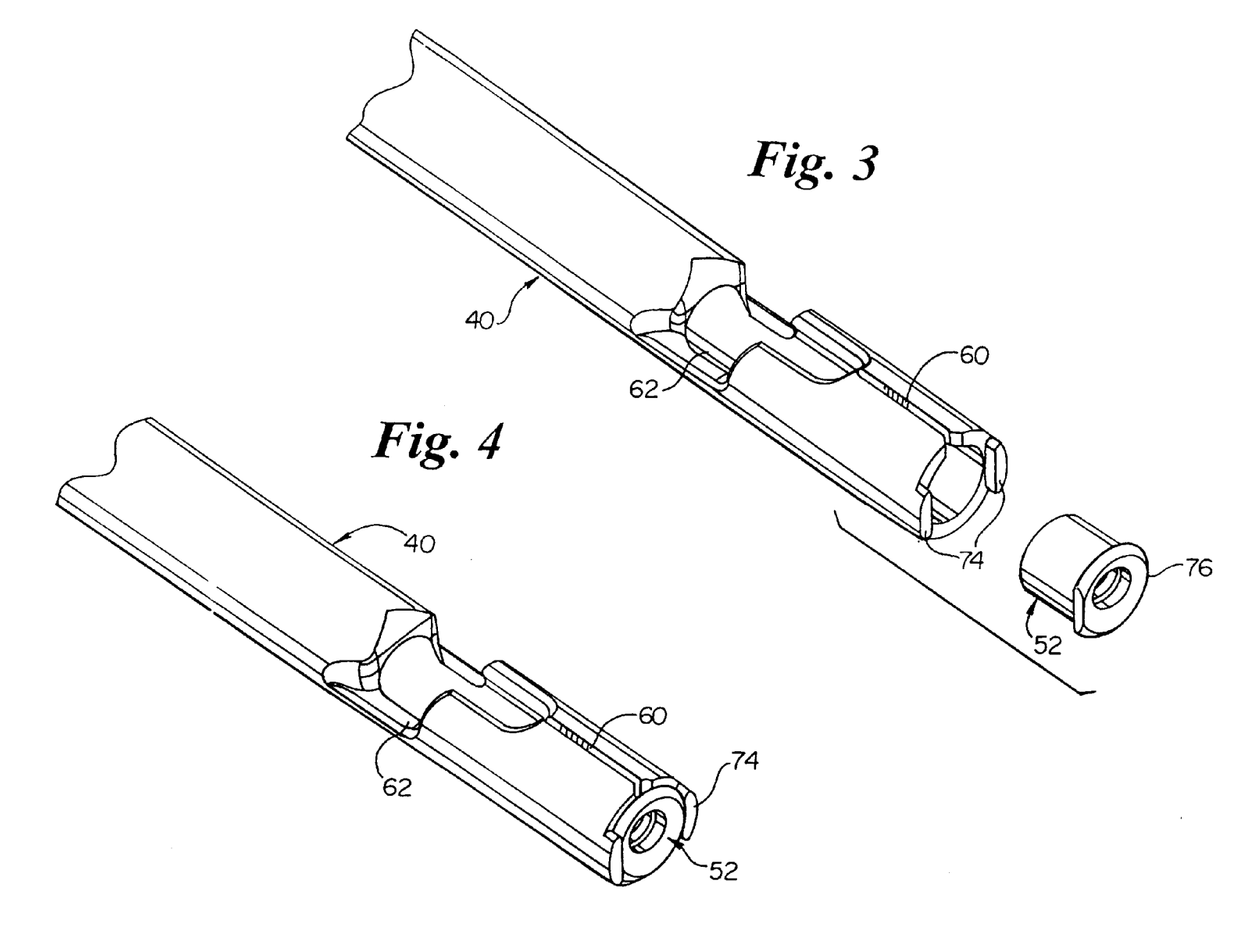
FIG. 3 is an enlarged perspective view of the distal end of the tool with a clip.
FIG. 4 is an enlarged perspective view of the distal end of the tool with a clip loaded.
Figure 5:
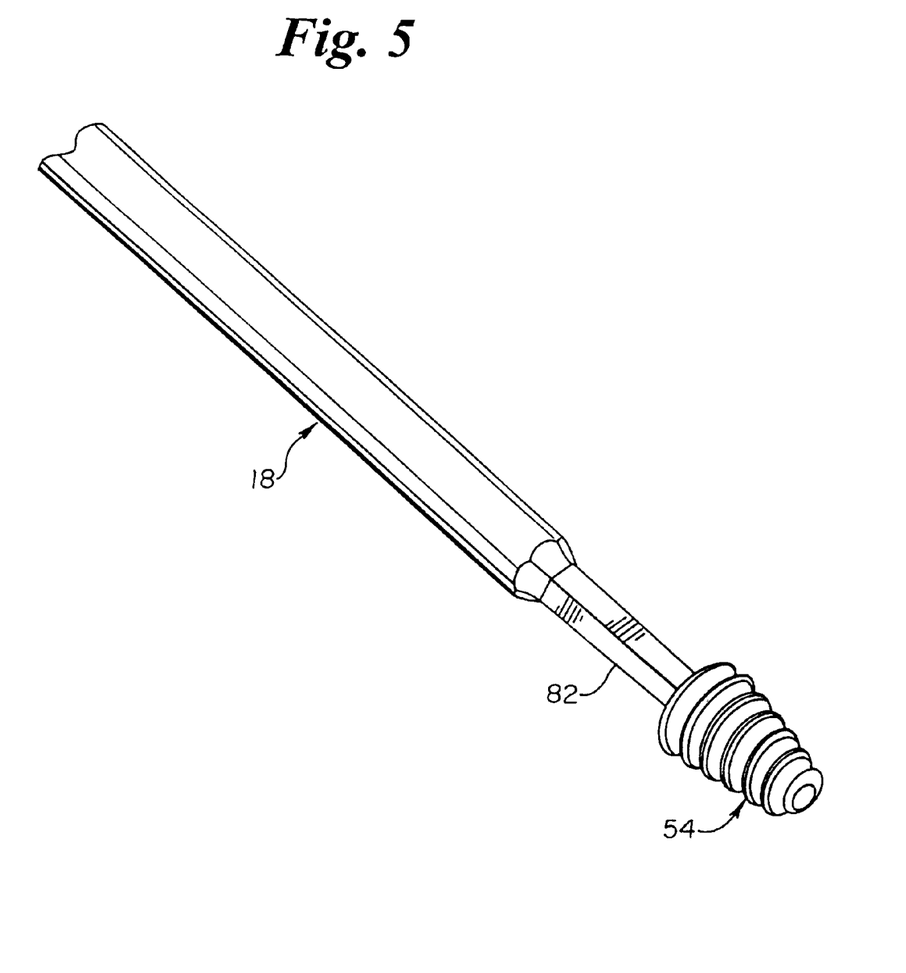
FIG. 5 is a partial perspective view of the screw wrench and screw assembled thereto.
Figures 6, 7:
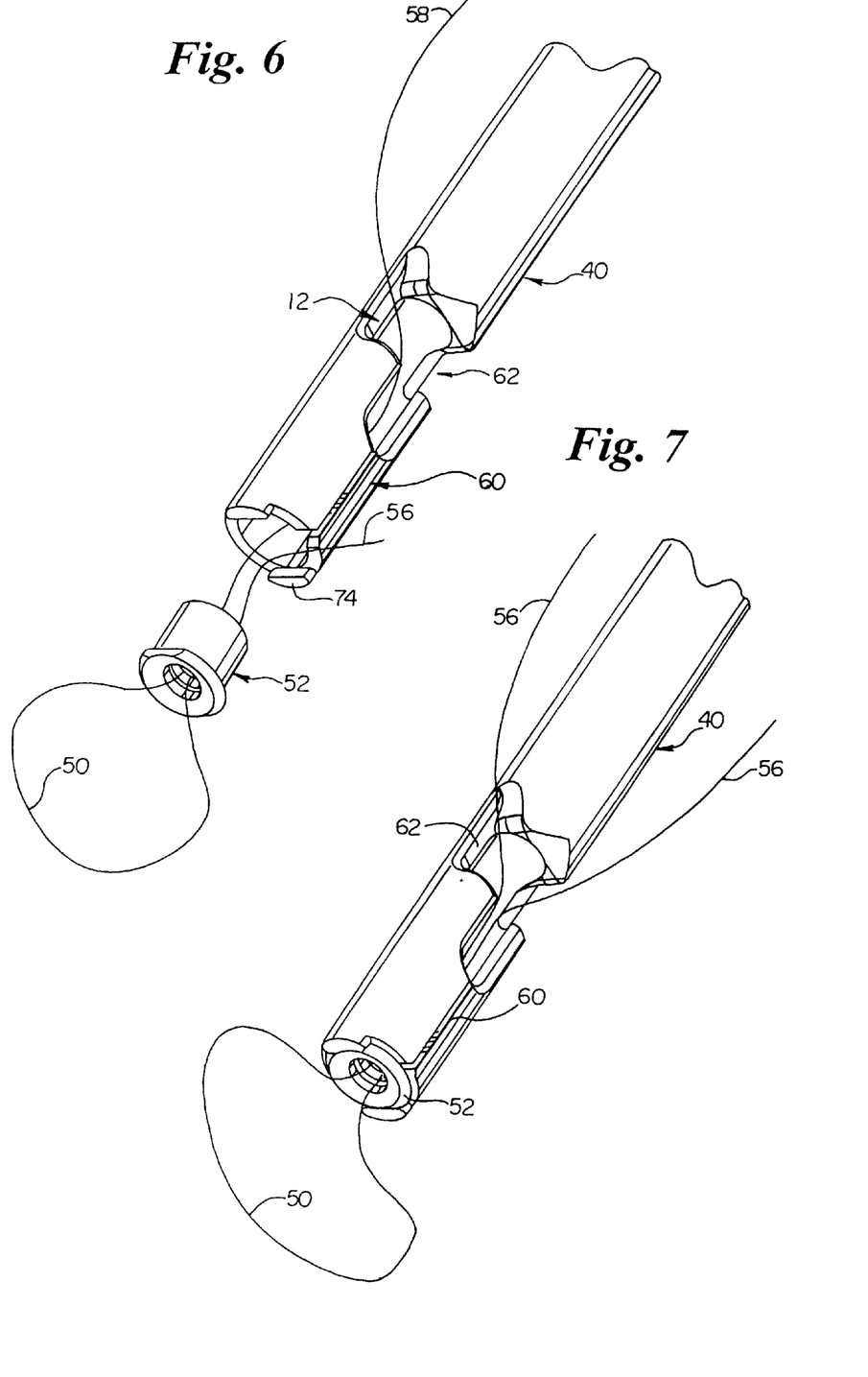
FIG. 6 is a perspective view of the distal end of the tool with a clip and cable passing into the tension shaft.
FIG. 7 is a perspective view of the distal end of the tool with a clip and cable passing into the tension shaft, with the clip held to the tool.
Figure 8:
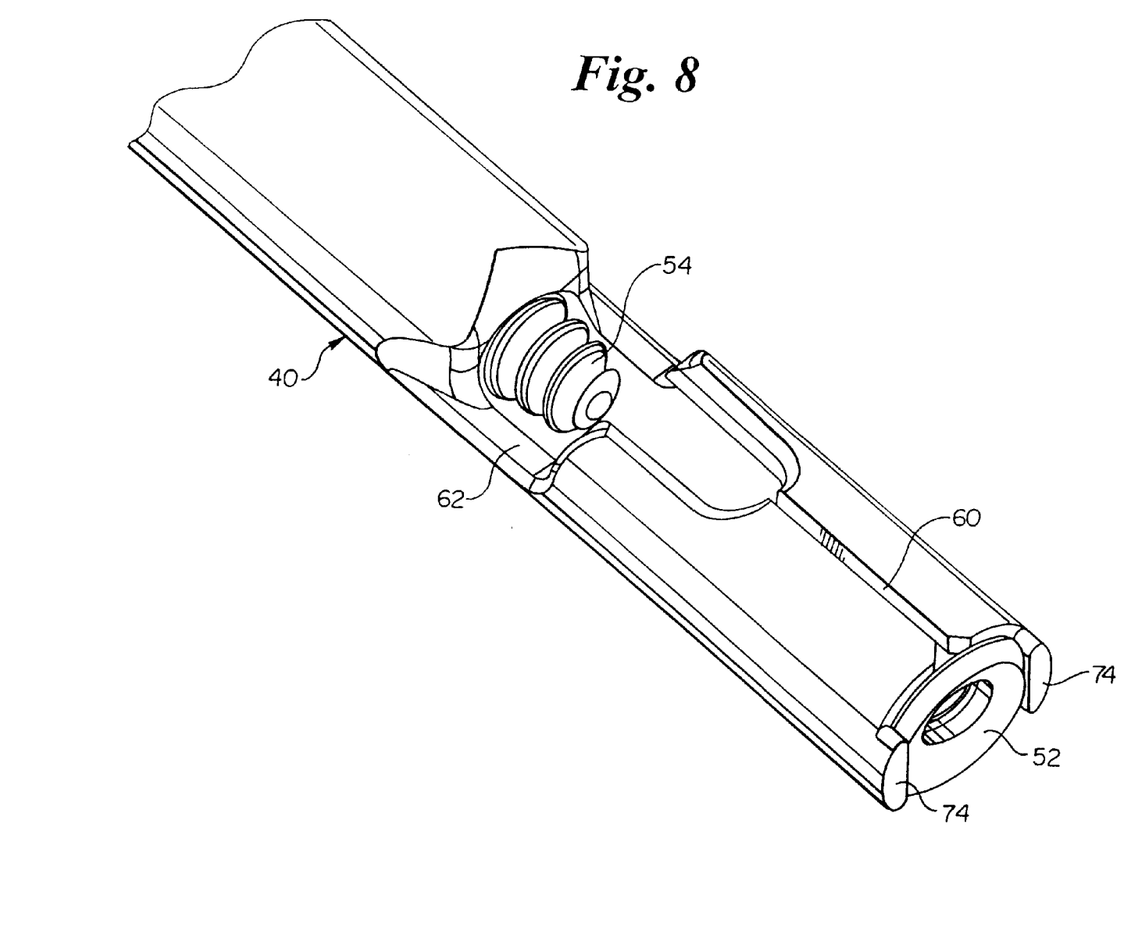
FIG. 8 is a perspective view of the distal end of the tool with the clip in place and a lock screw descending down.
Figure 9:
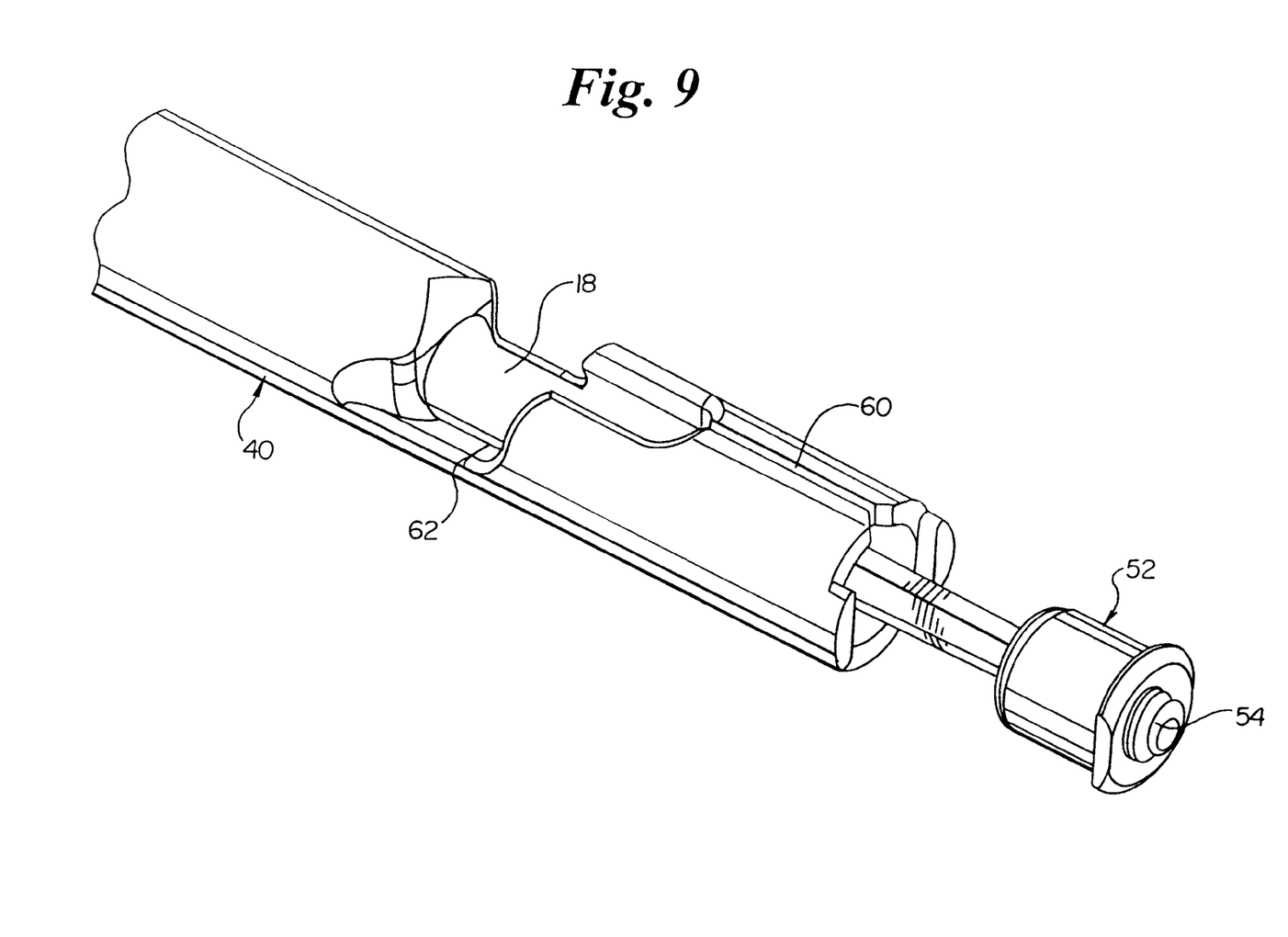
FIG. 9 is a perspective view of the distal end of the tool with the screw locked in the clip with the locked clip being ejected from the tool.
Figure 10:
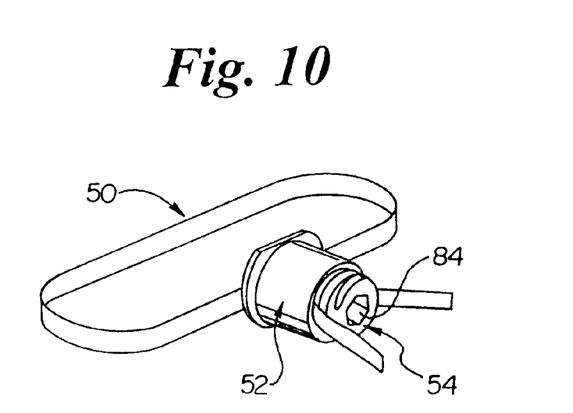
FIG. 10 is a perspective view showing a clip, screw and cable.
Figure 11:
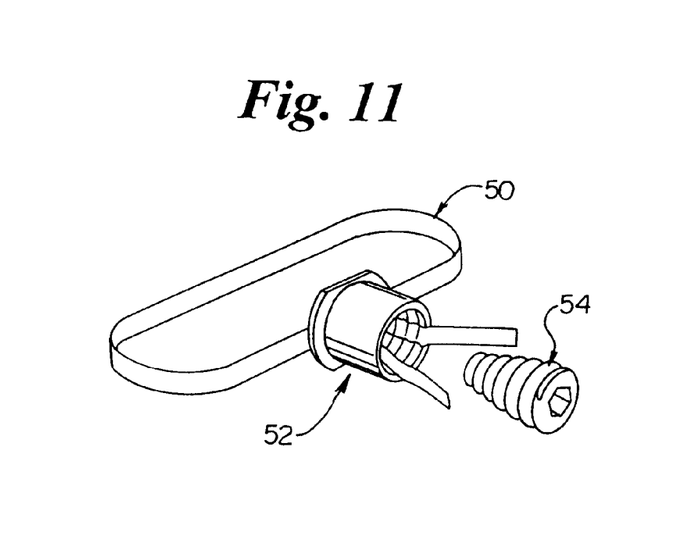
FIG. 11 is a view of the clip, screw and cable of FIG. 10 with the screw removed.
Figure 12:
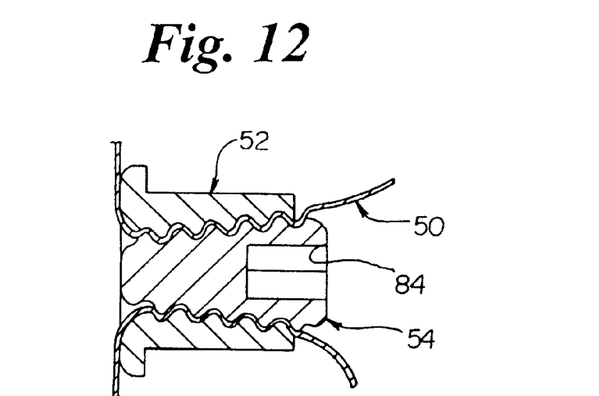
FIG. 12 is a cross-sectional view through an assembled clip and screw trapping a cable.

In operation, the tensioning tool 10 is preassembled with a clip 52 and tension band 50 (one end) prior to placing and routing the tension band 50 at the surgical site. As shown in FIG. 3, the tension shaft 40 has two tabs 74 which engage flats 76 on clip 52 which prevent the clip from rotating. The tensioning tool 10 holds one end of the tension band 50 and the clip 52 for placement into the patient's body with the surgeon guiding and routing the free end of the tension band 50. Once routed, the surgeon connects the free end of the tension band 50 to the tensioning tool 10 for final tensioning and locking with the clip screw lock 54. The tension band 50 is routed up to a slotted locking pin 78 and routed through the slot around the pin and back through the slot to secure it in place. The remaining free end of the tension band 50 and the tension tool 10 is placed into the surgical site and the free end is routed around the desired structural elements (such as a around the vertebral spinous process, as shown in U.S. Pat. No. 5,989,256, the disclosure of which is incorporated herein by reference). The free end is then routed through the clip 52 entrance and up to the other slotted locking pin 80 and is secured as described for the other end to pin 80.

Tensioning is accomplished by turning the adjusting knob 16 clockwise which drives the tension shaft 40 out of the tension body 12. This increases the length between the slotted locking pins 78, 80 and the end of the tensioning shaft 40 thereby pulling the tension band 50 through the clip 52. The clip screw 54 is placed on the end of tension wrench 18 which has a tapered hex male end 82 which makes a frictional fit with the clip screw female hex end 84. The tension wrench 18 with screw 54 in position is slid through tension tool 10 from the adjusting knob end. The clip screw 54 is screwed into clip 52 locking the tension band 50 within the clip. Once locked, the adjusting knob 16 may be turned counter-clockwise to loosen the tension band 50 on the tensioning tool 10. The tension wrench 18 may then be pushed to eject the locked clip 52 from the end of the tension shaft 40. The tension tool 10 is removed and any excess tension band 50 may be cut away.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A tensioning tool for applying tension to a tension band held between a clip and a clip screw, the tension tool including a body having fixed positions for attaching ends of a tension band, a tension shaft having a proximal and a distal end and being constructed and arranged to hold a clip at its distal end and to be inserted through said body and attached at its proximal end to an adjusting mechanism which drives said tension shaft distally relative to said body, said tool further including a tension wrench for holding a screw and being constructed and arranged to pass through said tool proximally toward the distal end to thread a screw into a clip held at the distal end of said shaft.

2. The tensioning tool of claim 1 wherein said adjusting mechanism is a knob which is rotationally mounted to said body and said proximal end of said tension shaft is threaded into said knob such that rotation of said knob drives said shaft relative to said body.

3. The tensioning tool of claim 1 wherein said body fixed positions are slotted locking pins through which ends of a tension band may pass and be secured thereto.

4. The tensioning tool of claim 1 further including a side opening in said shaft adjacent said distal end such that a screw may be loaded onto said tension wrench.

5. The tensioning tool of claim 1 further including a tension spring within said body mechanism for displaying tension applied by the spring.

* * * * *